United States Patent
Raslambekov

(10) Patent No.: US 10,898,298 B1
(45) Date of Patent: Jan. 26, 2021

(54) SYSTEMS AND METHODS FOR DETERMINING ORTHODONTIC TREATMENT

(71) Applicant: Oxilio Ltd, Larnaca (CY)

(72) Inventor: Islam Khasanovich Raslambekov, Long Island City, NY (US)

(73) Assignee: Oxilio Ltd, Larnaca (CY)

( * ) Notice: Subject to any disclaimer, the term of this patent is extended or adjusted under 35 U.S.C. 154(b) by 0 days.

(21) Appl. No.: 16/843,401

(22) Filed: Apr. 8, 2020

(51) Int. Cl.
| | |
|---|---|
| *A61C 7/00* | (2006.01) |
| *A61B 6/14* | (2006.01) |
| *A61B 6/03* | (2006.01) |
| *A61B 6/00* | (2006.01) |
| *A61B 5/055* | (2006.01) |
| *G06T 7/00* | (2017.01) |
| *A61B 1/24* | (2006.01) |

(52) U.S. Cl.
CPC ............... *A61C 7/002* (2013.01); *A61B 1/24* (2013.01); *A61B 5/055* (2013.01); *A61B 6/032* (2013.01); *A61B 6/14* (2013.01); *A61B 6/5217* (2013.01); *G06T 7/0012* (2013.01); *G06T 2207/30008* (2013.01); *G06T 2207/30036* (2013.01)

(58) Field of Classification Search
CPC ......... A61B 6/14; A61B 6/032; A61B 5/4542; A61B 6/5247; A61C 9/0053; A61C 7/002; A61C 19/05; A61C 7/08; G06T 2207/30036; G06T 7/0014; G06T 7/74
See application file for complete search history.

(56) References Cited

U.S. PATENT DOCUMENTS

| | | | |
|---|---|---|---|
| 9,439,608 B2 | 9/2016 | Schutyser et al. | |
| 10,052,180 B1* | 8/2018 | Richter | ................ A61C 19/045 |
| 2007/0207441 A1 | 9/2007 | Lauren | |
| 2013/0328869 A1* | 12/2013 | Choi | ....................... G06T 19/20 |
| | | | 345/419 |
| 2016/0008096 A1 | 1/2016 | Wu et al. | |
| 2016/0128624 A1 | 5/2016 | Matt | |
| 2017/0143445 A1 | 5/2017 | Abkai | |

(Continued)

FOREIGN PATENT DOCUMENTS

| | | |
|---|---|---|
| RU | 2610531 C1 | 2/2017 |
| WO | 2012112069 A1 | 8/2012 |

(Continued)

OTHER PUBLICATIONS

Yang, "Building Anatomically Realistic Jaw Kinematics Model from Data", The Visual Computer 35(3) 1105-1118, May 2019.

(Continued)

*Primary Examiner* — Ross Varndell
(74) *Attorney, Agent, or Firm* — BCF LLP

(57) ABSTRACT

Methods and systems for determining an orthodontic treatment for a patient are provided. The method comprises: receiving image data associated with a patient's skull; identifying, based on the image data, a first pair of reference pints; identifying, based on the image data, a second pair of reference points; generating based on the first and second pairs of reference points a first reference line and the second reference line, respectively; determining, based on an intersection of the first reference line and the second reference line, a rotation center of a patient's mandible; and based on the rotations center, determining the orthodontic treatment for the patient.

14 Claims, 8 Drawing Sheets

(56) References Cited

U.S. PATENT DOCUMENTS

| | | | |
|---|---|---|---|
| 2017/0265977 A1 | 9/2017 | Fisker et al. | |
| 2017/0312064 A1 | 11/2017 | Jaisson et al. | |
| 2017/0325909 A1 | 11/2017 | Gao | |
| 2018/0005377 A1 | 1/2018 | Alvarez et al. | |
| 2018/0122089 A1 | 5/2018 | Kim et al. | |
| 2018/0263731 A1* | 9/2018 | Pokotilov | G06T 17/20 |
| 2018/0263732 A1* | 9/2018 | Pokotilov | G06T 17/20 |
| 2018/0263733 A1* | 9/2018 | Pokotilov | G06T 17/20 |
| 2018/0344437 A1* | 12/2018 | Richter | A61C 19/045 |
| 2019/0026910 A1 | 1/2019 | Dekel et al. | |
| 2019/0029522 A1 | 1/2019 | Sato et al. | |
| 2020/0035351 A1* | 1/2020 | Kim | G06K 9/6267 |
| 2020/0085535 A1* | 3/2020 | Pokotilov | A61C 7/08 |

FOREIGN PATENT DOCUMENTS

| | | |
|---|---|---|
| WO | 2012112070 A1 | 8/2012 |
| WO | 2017149010 A1 | 9/2017 |
| WO | 2018035524 A1 | 2/2018 |

OTHER PUBLICATIONS

Abdelrahim, "Three-Dimensional Modeling of the Human Jaw/Teeth Using Optics and Statistics", University of Louisville, 2014, Electronic Theses and Dissertations. Paper 3.

Valinoti, "The Hinge-Axis Angle", Journal of Clinical Orthodonics (Aug. 1977), retrieved from https://www.jco-online.com/archive/1977/08/551/ on Jan. 9, 2020.

Rekow, "Location of the Mandibular Center of Autorotation in Maxillary Impaction Surgery", Am J Orthod Dentofacial Orthop. Jun. 1993;103(6):530-6.

Nadjmi, "Prediction of Mandibular Autorotation", Journal of Oral and Maxillofacial Surgery, vol. 56, Issue 11, 1241-1247 Nov. 1998.

Kim, "Prediction of Mandibular Movement and its Center of Rotation for Nonsurgical Correction of Anterior Open Bite via Maxillary Molar Intrusion", The Angle Orthodontist: Sep. 2018, vol. 88, No. 5, pp. 538-544.

Hosseinzadeh Nik, "A Retrospective Cephalometric Evaluation on Location of Center of Mandibular Autorotation after Le Fort I Superior Repositioning Osteotomy", Iranian Journal of Orthodontics, vol. 9, 2014, 37-42.

* cited by examiner

SYSTEMS AND METHODS FOR DETERMINING ORTHODONTIC TREATMENT

FIELD

The present technology relates to systems and methods for determining an orthodontic treatment for a patient, in general; and more specifically to determining a rotation axis for a mandibular jaw of a patient for determining the orthodontic treatment.

BACKGROUND

For devising a new orthodontic treatment for a malocclusion disorder of a patient (or for assessing efficacy of already an existent one) aimed at a specific malocclusion disorder of a patient, practitioners typically use various anthropometric parameters associated with a patient's skull, determined through corresponding image data.

Some of these parameters may include those defining possible physical spatial motion and positions of a mandibular jaw within the patient's skull relative to his/her maxillary jaw, which are effectuated with an aid of his/her masticatories (chewing muscles). These specific parameters can be said to be indicative of articulation of the patient.

Specifically, considerations in assessing the articulation of the patient may include estimating certain angles of the mandibular jaw, for example, relative to the Frankfort horizontal plane associated with the patient's skull while a mandibular head (also referred to herein as "mandibular condyle") of the mandibular jaw is moving in a respective temporomandibular joint (TMJ), such as an incisal guidance angle, a sagittal condylar angle, a Bennet angle, and the like. Accordingly, for a more accurate determination of these angles, it is first necessary to accurately determine their vertex—a rotation center of the mandibular jaw, which is a geometric point in each respective mandibular head, through which a rotation axis of the mandibular jaw extends.

A more accurately determined rotation center of the mandibular jaw may thus allow a more realistic modelling of the articulation of the mandibular jaw of the patient, which could further enable the determination of a more efficient and effective orthodontic treatment plan (for example, through application of an orthodontic device or through surgery).

Certain prior art approaches have been proposed to address the above-identified technical problem of determining the rotation center of the mandibular jaw as an intersection of specifically constructed lines using image data associated with the patient's skull.

An article entitled "Location of the Mandibular Center of Autorotation in Maxillary Impaction Surgery", written by Rekow et al., and published by American Journal of Orthodontics and Dentofacial Orthopedics in 1993 discloses investigation focusing on the problems associated with locating that center of autorotation and identifies factors that can increase the probability of accurately identifying its location for predicting surgical outcomes. The reliability of the Rouleaux technique for calculating the centers of rotation is established and is shown to be acceptable, as long as the landmarks used for determining the center are properly selected, and the magnitude of the rotation required is sufficient. The location of the centers of autorotation of the mandibles after maxillary impaction surgery for 46 patients was used to investigate the errors associated with landmark selection and amounts of rotation. Although there is much variation in its location, the center does not lie within the body of the condyle but instead lies away from the condyle. Guidelines for maximizing the reliability of predicting surgical outcomes on the basis of autorotation of the mandible after maxillary impaction surgery are given.

An article entitled "The Hinge-Axis Angle", by Valinoti, and published by Journal of Clinical Orthodontics discloses constructing an angle around the hinge-axis that goes through both condyles and is formed by the intersection of two lines, the first being the Frankfort horizontal plane. The second line forming this angle is drawn from the condyle centers (the hinge axis passes approximately through these) to pogonion. The angle thus formed is Frankfort horizontal plane; hinge-axis point; hinge-axis pogonion line.

An article entitled "Prediction of Mandibular Autorotation", by Nadjmi et al., and published by the American Association of Oral and Maxillofacial Surgeons discloses testing prospectively the hypothesis that the center of mandibular rotation during initial jaw opening is the same as during impaction surgery. If so, individual determination of this center would provide a simple method to predict the final morphology of the nasal tip, upper lip, lower lip, chin, and cervicomental profile. This would aid in deciding preoperatively whether nasal tip surgery, total mandibular surgery, a genioplasty, or submental liposuction should complement the maxillary impaction procedure.

An article entitled "Prediction of Mandibular Movement and its Center of Rotation for Nonsurgical Correction of Anterior Open Bite via Maxillary Molar Intrusion", by Kim et al. discloses calculating center of mandibular autorotation by measuring displacement of gonion (Go) and pogonion (Pog). Paired t-tests were used to compare variables, and linear regression analysis was used to examine the relationship between AU6-PP and other variables.

U.S. Patent Application Publication No.: 2007/207441-A1 published on Sep. 6, 2007, assigned to Great Lakes Orthodontics Ltd, and entitled "Four Dimensional Modeling of Jaw and Tooth Dynamics" discloses methods and systems to digitally model the 4-dimensional dynamics of jaw and tooth motion using time-based 3-dimensional data. Complete upper and lower digital models are registered to time-based 3-dimensional intraoral data to produce a true 4-dimensional model. Diagnostic and clinical applications include balancing the occlusion and characterizing the geometry of the temporomandibular joint. The 4-dimensional model is readily combined with conventional imaging methods such as CT to create a more complete virtual patient model.

SUMMARY

It is an object of the present technology to ameliorate at least some of the inconveniences present in the prior art.

The developers of the present technology have realized that the movement associated with the mandibular jaw relative to the given patient's Frankfort horizontal plane may be projected more realistically if the rotation center of the mandibular jaw is determined as an intersection of at least two reference lines generated based on an analysis of a 2D lateral projection of the patient's skull.

Specifically, the developers of the present technology have appreciated that each of these at least two reference lines may be generated based on a respective pair of reference points, identified in the lateral projection of the patient's skull, that are indicative of muscle attachments of muscles involved in effectuating movements of the patient's mandibular jaw, thereby accounting for individual features of the patient. In particular, developers have appreciated that accounting for both rotational and translational components of mandibular joint movement, through reference points relating to muscles used in rotational and translational movement, may contribute to modelling a more realistic movement.

Thus, the rotation center of the mandibular jaw determined as an intersection of the so generated lines may allow for modelling a more realistic movement thereof. Particularly, certain non-limiting embodiments of the present technology may allow for determining the rotation center of the mandibular jaw that is not located in the center of the mandibular head, which may allow for effectively accounting for both components of the mandibular movement—rotational and translational.

Further, using the 2D lateral projection of the patient's skull for identifying the reference points and generating the lines allows for a more efficient, in terms of computational resources, method for determining the rotation center as there is no need for obtaining and further processing additional 3D scans (such as CT/magnetic resonance scans).

Accordingly, data of the rotation center of the mandibular jaw determined according to the non-limiting embodiments of the present technology is believed to help to determine a more efficient and effective orthodontic treatment plan for the patient.

Therefore, according to one broad aspect of the present technology, there is provided a method for determining an orthodontic treatment for a patient. The method is executable by a processor. The method comprises: receiving image data associated with an image of a skull of the patient, the image data including data relating to a mandibular portion and a cranium portion of the skull; identifying, from the image data, a first pair of reference points for defining a first reference line, the first pair of reference points including a first point on the mandibular portion and a second point on the cranium portion of the skull of the patient; identifying, from the image data, a second pair of reference points for defining a second reference line, the second pair of reference points including third and fourth points on the cranium portion of the skull; the second reference line intersecting with the first reference line; generating, based on the first pair of reference points, the first reference line; generating, based on the second pair of reference points, the second reference line; determining, based on an intersection of the first reference line and the second reference line, a rotation center for a patient's mandible; determining, based on the rotation center of the patient's mandible, the orthodontic treatment for the patient.

In some implementations of the method, the first point of the first pair of reference points comprises an Articulare point, and the second point of the first pair of reference points comprises a Gnathion point.

In some implementations of the method, the third point of the second pair of reference points comprises a Basion point, and the fourth point of the second pair of reference points comprises an Orbitale point.

In some implementations of the method, the first point of the first pair of reference points comprises the Articulare point, the second point of the first pair of reference points comprises the Gnathion point, the third point of the second pair of reference points comprises the Basion point, and the fourth point of the second pair of reference points comprises the Orbitale point.

In some implementations of the method, the identifying the first and second pairs of reference points comprises conducting a cephalometric analysis of the image data.

In some implementations of the method, the cephalometric analysis comprises processing the image data based on one or more of: image segmentation, image alignment, facial landmark detection, and predetermined relative positions between anatomical landmarks.

In some implementations of the method, the image comprises one or more of: a radiograph, a photograph, a CT scan, a dental model, and a magnetic resonance image.

In some implementations of the method, the image is a lateral image of a first side of the skull of the patient.

In some implementations of the method, the rotation center is a first rotation center of the first side of the skull of the patient, and wherein the method further comprises determining a second rotation center based on an image of a second side of the skull of the patient, and wherein the determining the orthodontic treatment is based on the first rotation and the second rotation center.

In some implementations of the method, the rotation center is not a center of a mandibular head.

In some implementations of the method, the method further comprises sending instructions to display, on a screen, the image of at least a portion of the skull and including the rotation center of the mandible.

From another aspect, there is provided a method for generating a visualization of a skull of a patient including a rotation center of a mandible, the method being executable by a processor, the method comprising: receiving image data, the image data being associated with an image of the skull of the patient, the image data including data relating to a mandibular portion and a cranium portion of the skull; identifying, from the image data, a first pair of reference points for defining a first reference line, the first pair of reference points including a first point on the mandibular portion and a second point on the cranium portion of the skull of the patient; identifying, from the image data, a second pair of reference points for defining a second reference line, the second pair of reference points including a third and fourth points on the cranium portion of the skull; the second reference line intersecting with the first reference line; generating, based on the first pair of reference points, the first reference line; generating, based on the second pair of reference points, the second reference line; determining, based on an intersection of the first reference line and the second reference line, a rotation center for a patient's mandible; sending instructions to display, on a screen, the image of the skull including the rotation center for the patient's mandible.

According to another broad aspect of the present technology, there is provided a system for determining an orthodontic treatment for a patient. The system comprises a computer system having a processor. The processor is arranged to execute a method comprising: receiving image data associated with an image of a skull of the patient, the image data including data relating to a mandibular portion and a cranium portion of the skull; identifying, from the image data, a first pair of reference points for defining a first reference line, the first pair of reference points including a first point on the mandibular portion and a second point on the cranium portion of the skull of the patient; identifying, from the image data, a second pair of reference points for defining a second reference line, the second pair of reference points including third and fourth points on the cranium portion of the skull; the second reference line intersecting with the first reference line; generating, based on the first pair of reference points, the first reference line; generating, based on the second pair of reference points, the second reference line; determining, based on an intersection of the first reference line and the second reference line, a rotation center for a patient's mandible; determining, based on the rotation center of the patient's mandible, the orthodontic treatment for the patient.

In some implementations of the system, the first point of the first pair of reference points comprises an Articulare point, and the second point of the first pair of reference points comprises a Gnathion point.

In some implementations of the system, the third point of the second pair of reference points comprises a Basion point, and the fourth point of the second pair of reference points comprises an Orbitale point.

In some implementations of the system, the first point of the first pair of reference points comprises the Articulare point, the second point of the first pair of reference points comprises the Gnathion point, the third point of the second pair of reference points comprises the Basion point, and the fourth point of the second pair of reference points comprises the Orbitale point.

In some implementations of the system, the identifying the first and second pairs of reference points comprises conducting a cephalometric analysis of the image data.

In some implementations of the system, the cephalometric analysis comprises processing the image data based on one or more of: image segmentation, image alignment, facial landmark detection, and predetermined relative positions between anatomical landmarks.

In some implementations of the system, the image comprises one or more of: a radiograph, a photograph, a CT scan, a dental model, and a magnetic resonance image.

In some implementations of the system, the image is a lateral image of a first side of the skull of the patient.

In some implementations of the system, the rotation center is a first rotation center of the first side of the skull of the patient, and wherein the system further comprises determining a second rotation center based on an image of a second side of the skull of the patient, and wherein the determining the orthodontic treatment is based on the first rotation and the second rotation center.

In some implementations of the system, the rotation center is not a center of a mandibular head.

According to another aspect, there is provided a system for generating a visualization of a skull of a patient including a rotation center of a mandible, the system comprising: a screen on which the visualization of the skull of the patient including the rotation center of the mandible is displayed, and a processor connected to the screen and arranged to execute, the method comprising: receiving image data, the image data being associated with an image of a skull of the patient, the image data including data relating to a mandibular portion and a cranium portion of the skull; identifying, from the image data, a first pair of reference points for defining a first reference line, the first pair of reference points including a first point on the mandibular portion and a second point on the cranium portion of the skull of the patient; identifying, from the image data, a second pair of reference points for defining a second reference line, the second pair of reference points including a third and fourth points on the cranium portion of the skull; the second reference line intersecting with the first reference line; generating, based on the first pair of reference points, the first reference line; generating, based on the second pair of reference points, the second reference line; determining, based on an intersection of the first reference line and the second reference line, a rotation center for a patient's mandible; sending instructions to display, on a screen, the image of the skull including the rotation center for the patient's mandible.

In the context of the present specification, unless expressly provided otherwise, a computer system may refer, but is not limited to, an "electronic device", an "operation system", a "system", a "computer-based system", a "controller unit", a "control device" and/or any combination thereof appropriate to the relevant task at hand.

In the context of the present specification, unless expressly provided otherwise, the expression "computer-readable medium" and "memory" are intended to include media of any nature and kind whatsoever, non-limiting examples of which include RAM, ROM, disks (CD-ROMs, DVDs, floppy disks, hard disk drives, etc.), USB keys, flash memory cards, solid state-drives, and tape drives.

In the context of the present specification, a "database" is any structured collection of data, irrespective of its particular structure, the database management software, or the computer hardware on which the data is stored, implemented or otherwise rendered available for use. A database may reside on the same hardware as the process that stores or makes use of the information stored in the database or it may reside on separate hardware, such as a dedicated server or plurality of servers.

In the context of the present specification, unless expressly provided otherwise, the words "first", "second", "third", etc. have been used as adjectives only for the purpose of allowing for distinction between the nouns that they modify from one another, and not for the purpose of describing any particular relationship between those nouns.

Embodiments of the present technology each have at least one of the above-mentioned object and/or aspects, but do not necessarily have all of them. It should be understood that some aspects of the present technology that have resulted from attempting to attain the above-mentioned object may not satisfy this object and/or may satisfy other objects not specifically recited herein.

Additional and/or alternative features, aspects and advantages of embodiments of the present technology will become apparent from the following description, the accompanying drawings and the appended claims.

BRIEF DESCRIPTION OF THE DRAWINGS

For a better understanding of the present technology, as well as other aspects and further features thereof, reference is made to the following description which is to be used in conjunction with the accompanying drawings, where.

DETAILED DESCRIPTION

Certain aspects and embodiments of the present technology are directed to methods of and systems for determining movements of a mandibular jaw of a patient in a TMJ indicative of patient's articulation, and further, based thereon, determining an orthodontic treatment plan for the patient. According to the non-limiting embodiments of the present technology, determining the treatment plan for the patient may further include, depending on a specific orthodontic problem of the patient, determining a new treatment plan, or determining a following stage of treatment by dynamically assessing efficacy of a current treatment plan, for example.

Further, it should be expressly understood that, in the context of the present specification, the term "orthodontic treatment" is broadly referred to as any type of medical intervention aimed at correcting malocclusions associated with the patient, including surgical and non-surgical manipulations, such as, but not limited to, using aligners. Further, the orthodontic treatment, as referred to herein, may be determined by a professional practitioner in the field of dentistry (such as orthodontist, a maxillofacial surgeon, for example), or automatically by a specific piece of software, based on respective image data and input parameters associated with the patient.

More specifically, certain aspects and embodiments of the present technology comprise a computer-implemented method for determining a rotation center of the mandibular jaw (also referred to herein as "mandible") in an associated mandibular head (also referred to herein as "condylar head" and "mandibular condyle") in the TMJ. Further, based on at least one so determined rotation center, a horizontal rotation axis of the mandible may be determined, which further defines certain movements of the mandible.

Certain non-limiting embodiments of the present technology minimize, reduce or avoid some of the problems noted in association with the prior art. For example, by implementing certain embodiments of the present technology in respect of the rotation center of the mandible, one or more of the following advantages may be obtained: a more efficient and individualized approach to determining mandibular movements on a 3D model of patient's arch forms for determining the orthodontic treatment plan for him/her. This is achieved in certain non-limiting embodiments of the present technology by direct projecting so-determined rotation center and the rotation axis onto the 3D model of patient's arch forms without taking additional 3D scans (such as computed tomography scans). In this regard, methods and systems provided herein, according to certain non-limiting embodiments of the present technology, allow achieving a higher accuracy and stability in diagnostics of malocclusions, and consequently, devising more efficient and effective orthodontic treatment plans.

3D Model

Figure 1:
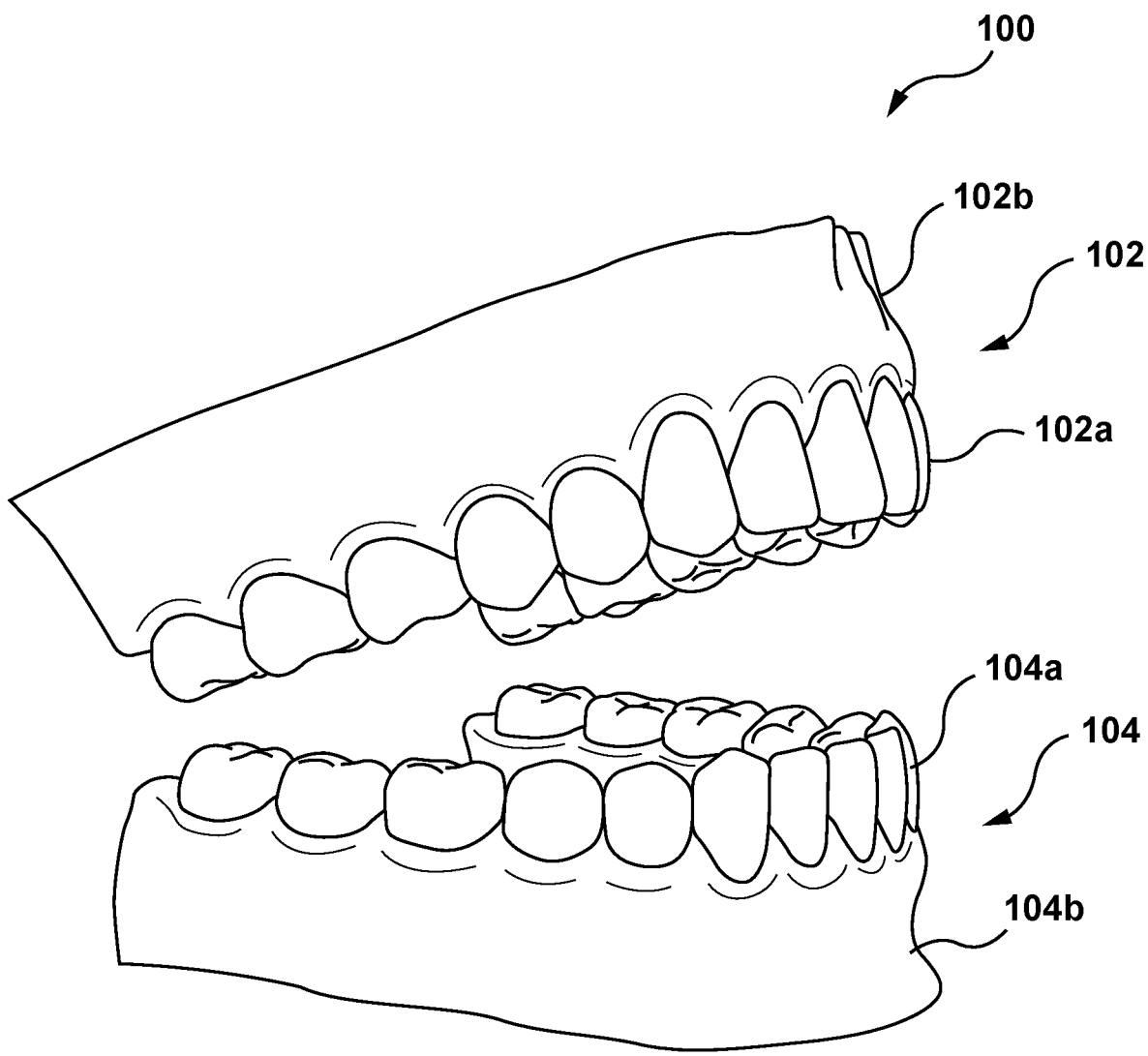
FIG. 1 depicts a perspective view of a 3D model of an upper arch form and a lower arch form of a subject, according to the non-limiting embodiments of the present technology.

Referring initially to FIG. 1, there is depicted a view of a 3D model 100 representing a current configuration of an upper arch form 102 (also referred to herein as "maxillary arch form") and a lower arch form 104 (also referred to herein as "mandibular arch form") of a subject (also referred to herein as "patient", not depicted), in accordance with the non-limiting embodiments of the present technology.

According to the non-limiting embodiments of the present technology, the upper arch form 102 comprises upper teeth 102a and upper gum 102b, and the lower arch form 104 comprises lower teeth 104a and lower gum 104b.

It should be expressly understood that methods of obtaining the 3D model 100 are not limited and may include, in certain non-limiting embodiments of the present technology, computed tomography-based scanning of the upper arch forms 102 and lower arch form 104 of the subject, for example, using a cone beam computed tomography (CBCT) scanner. Generally speaking, the CBCT scanner comprises software and hardware allowing for capturing data using a cone-shaped X-ray beam by rotating around the subject's head. This data may be used to reconstruct 3D representations of the following regions of the subject's anatomy: dental (teeth and gum, for example); oral and maxillofacial region (mouth, jaws, and neck); and ears, nose, and throat ("ENT"). Accordingly, the CBCT scanner, depending on the task at hand, may allow not only for obtaining the 3D representations of the upper arch from 102 and the lower arch form 104, but also deeper bone structures, such as a maxilla and a mandible of the subject respectively associated therewith, as well as certain cranial structures, such as, for example, temporal bones and the temporomandibular joints (TMJ).

In a specific non-limiting example, the CBCT scanner can be of one of the types available from 3Shape, Private Limited Company of Holmens Kanal 7, 1060 Copenhagen, Denmark. It should be expressly understood that the CBCT scanner can be implemented in any other suitable equipment.

In other non-limiting embodiments of the present technology, the 3D model 100 may be obtained via intraoral scanning, by applying an intraoral scanner, enabling to capture direct optical impressions of the upper arch form 102 and the lower arch form 104.

In a specific non-limiting example, the intraoral scanner can be of one of the types available from MEDIT, corp. of 23 Goryeodae-ro 22-gil, Seongbuk-gu, Seoul, Korea. It should be expressly understood that the intraoral scanner can be implemented in any other suitable equipment.

In yet other non-limiting embodiments of the present technology, the 3D model 100 may be obtained via scanning molds representing the upper arch from 102 and the lower arch form 104. In this regard, the molds may have been obtained via dental impression using a material (such as a polymer, e.g. polyvinyl-siloxane) having been imprinted with the shape of the intraoral anatomy it has been applied to. In the dental impression, a flowable mixture (i.e., dental stone powder mixed with a liquid in certain proportions) may be flowed such that it may, once dried and hardened, form the replica. The replica may then be retrieved from the dental impression and digitized by a desktop scanner to generate the 3D model 100.

In a specific non-limiting example, the desktop scanner can be of one of the types available from Dental Wings, Inc. of 2251, ave Letourneux, Montreal (QC), Canada, H1V 2N9. It should be expressly understood that the desktop scanner can be implemented in any other suitable equipment.

According to the non-limiting embodiments of the present technology, the 3D model 100 is used for determining an orthodontic treatment for the subject. In this regard, according to the non-limiting embodiments of the present technology, the orthodontic treatment may be determined based on data indicative of how the lower arch form 104 moves relative to the upper arch form 102; specifically, as an example, how the lower teeth 104a move relative to the upper teeth 102a. In a sense, these movements may, at least partially, define articulation of the mandible of the subject (such as a mandible 204 depicted in FIG. 2).

In the context of the present specification the term "articulation" is broadly referred to as all possible physical spatial movements of the mandible 204 relative to a maxilla of the subject (such as a maxilla 202 depicted in FIG. 2), and effectuated by respective masticatories when the subject is involving the mandible 204 in implementing a physiological function, such as speaking or eating, for example, or otherwise moving the mandible 204. Examples of such movements include, without being limited to, rotational movements of the mandible 204, translational movements of the mandible 204, and transverse movements of the mandible 204 in various planes of a subject's skull (such as a skull 200 depicted in FIG. 2).

Mandible Articulation

Generally speaking, when the mandible 204 of the subject is involved in implementing one or more physiological functions, the mandible 204 may perform several movements, in one or more planes of the skull 200, simultaneously, depending on a specific phase of performing the physiological function. This may result in a total movement of the mandible 204 being very complex. Thus, for illustrative purposes only, below are provided examples in respect of translational and rotational movements of the mandible 204 in a sagittal plane of the skull 200.

Figure 2:
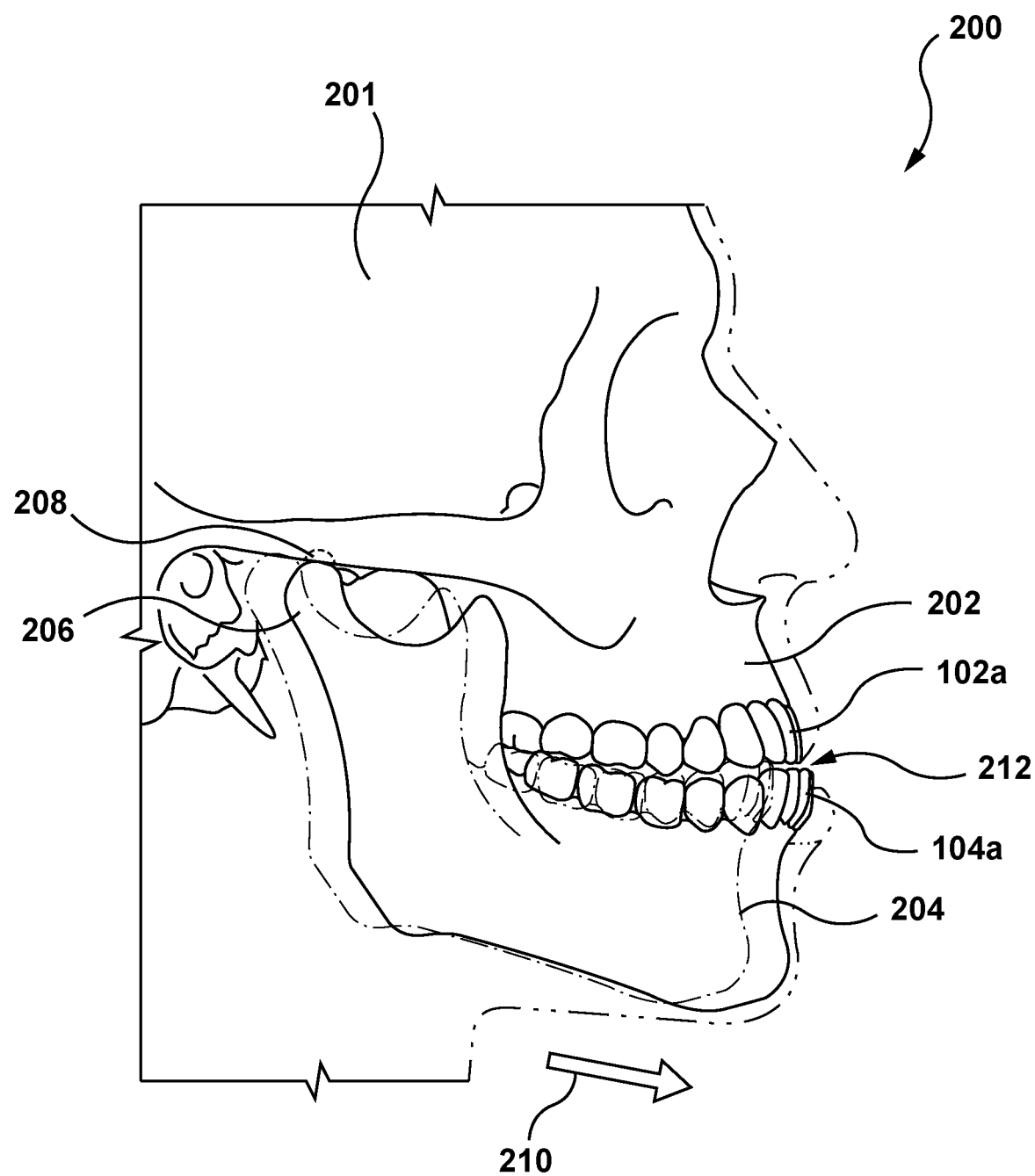
FIGS. 2 to 4 depict schematic diagrams of example movements of a mandibular jaw of the subject while performing a physiological function associated with opening his/her mouth, according to certain embodiments of the present technology.
Figure 3:
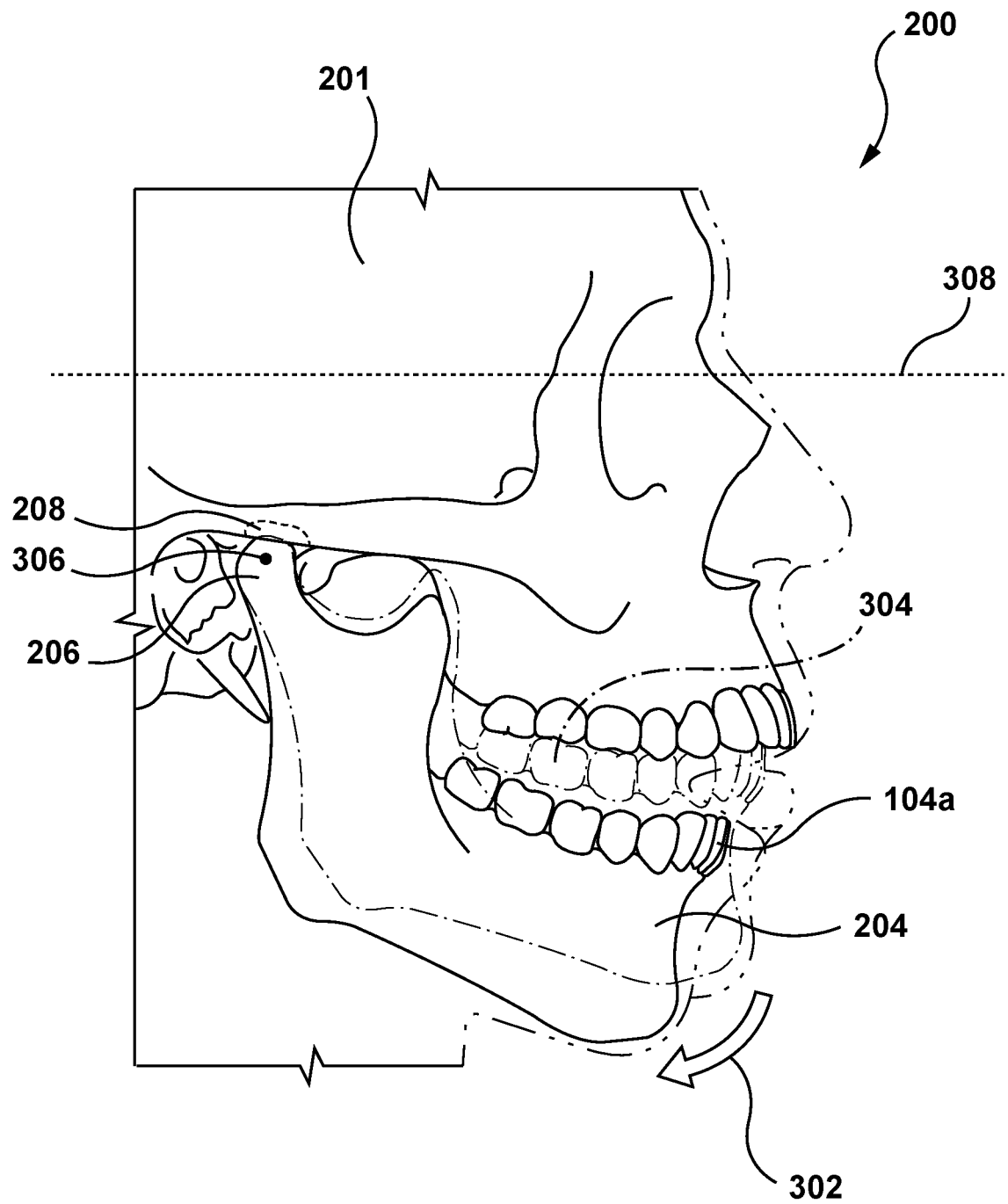
Figure 4:
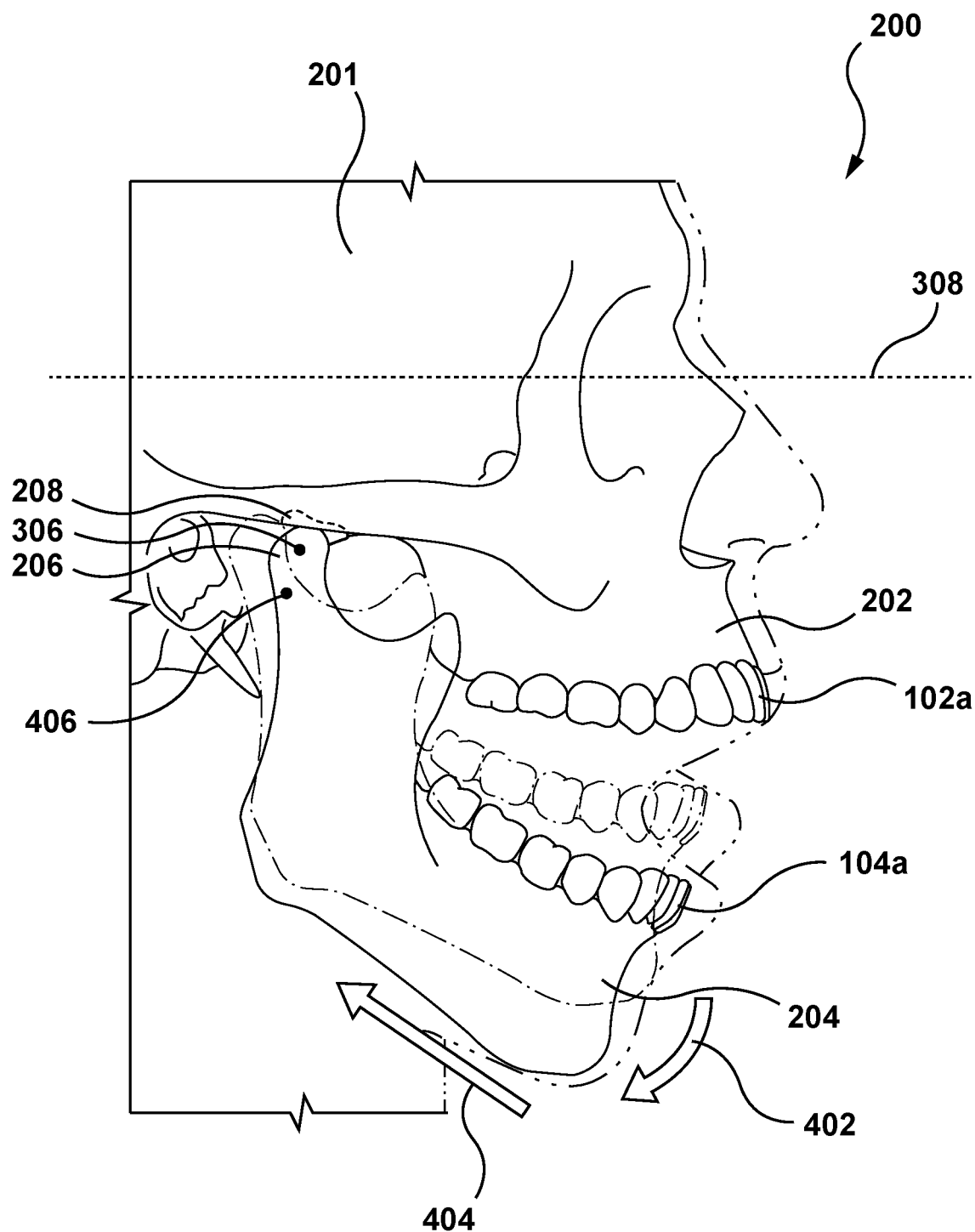

With reference to FIGS. 2 to 4, there is schematically depicted the sagittal plane of the skull 200 of the subject for demonstrating certain movements of the mandible 204 defining, at least partially, the articulation thereof when the subject is opening his/her mouth, in accordance with the non-limiting embodiments of the present technology.

Broadly speaking, the skull 200 comprises a cranial portion 201 (that is, an unmovable portion thereof) and the mandible 204 (that is, a movable portion thereof). The cranial portion 201 further comprises the maxilla 202 with the upper teeth 102a. The mandible 204 further comprises the lower teeth 104a and a mandibular head 206. Generally speaking, movements of the mandible 204 relative to the maxilla 202 are enabled by a TMJ 208.

With reference to FIG. 2, there is depicted a schematic diagram of the mandibular head 206 performing a translational movement in the TMJ 208. For example, the translational movement of the mandibular head 206 occurs when lower anterior teeth of the lower teeth 104a are sliding down internal surface of upper anterior teeth of the upper teeth 102a until they reach a position of being edge to edge to each other producing a temporary underbite 212. Typically, this translational movement, in the sagittal plane of the skull 200, occurs when the subject is starting opening his/her mouth and results in the mandible 204 moving translationally in a first translation direction 210.

With reference to FIG. 3, there is depicted a schematic diagram of the mandibular head 206 performing a pure rotational movement (also referred to herein as "hinge movement") in the TMJ 208. For example, the hinge movement of the mandibular head 206 may occur during a phase where the subject is continuing opening his/her mouth until the anterior teeth of the upper teeth 102a and the lower teeth 104a are around 20 to 25 mm apart in certain subjects. Consequently, the mandible 204 performs, in the sagittal plane of the skull 200, a rotational movement in a first rotation direction 302 around an axis extending through a geometric center 306 of the mandibular head 206 and parallel to a horizontal plane 308 of the skull 200.

However, when the subject is continuing opening his/her mouth to its maximum, where the anterior teeth of the upper teeth 102a and the lower teeth 104a are around 43 to 50 mm apart in certain subjects, a movement of the mandibular head 206 in the TMJ 208 during this phase may represent a superposition of rotational and translational movements. With reference to FIG. 4, there is depicted a schematic diagram of the subject opening its mouth to its maximum, which causes the mandibular head 206 to move, in the TMJ 208, rotationally downwards and translationally forwards. This movement of the mandibular head 206 is indicative of the mandible 204 moving downwards and backwards as indicated by a second rotation direction 402 and a second translation direction 404. Thus, it can be said that, in this phase of opening the mouth, for example, the mandible 204 performs, in the sagittal plane of the skull 200, a rotational movement around an axis extending through a rotation center 406 that is shifted from the geometric center 306 of the mandibular head 206.

Accordingly, the non-limiting embodiments of the present technology are directed to methods and systems for determining the rotation center 406, and hence the rotation axis determined based thereon, in the mandibular head 206 effectively accounting for rotational and translational movements of the mandibular head 206 in the TMJ 208.

Further, referring back to FIG. 1, according to the non-limiting embodiments of the present technology, the determined rotation center 406 and the rotation axis for the mandible 204 may be used for reproducing (in a sense, "animating" or modelling) movement of the lower arch form 104 relative to the upper arch form 102, thereby transferring the articulation movements of the mandible 204 onto the lower arch form 104.

Finally, according to the non-limiting embodiments of the present technology, the so reproduced movements of the lower arch form 104 relative to the upper arch form 102 may be used for determining the orthodontic treatment for the subject. For example, the reproduced movements of the lower arch form 104 may be used for determining certain diagnostic parameters, such as angles formed by the mandible 204 relative to a Frankfort horizontal plane associated with the skull 200 (not separately depicted) associated with the subject, including, but not being limited to, an incisal guidance angle, a sagittal condylar angle, a Bennet angle, and the like. Certain discrepancies of current values of these angles from their normal values may be indicative of specific malocclusion disorders, for treating which respective orthodontic treatment plans can be determined. How the rotation center 406 of the mandible 204 is determined will be described below with references to FIGS. 7 to 9.

System

Figure 5:
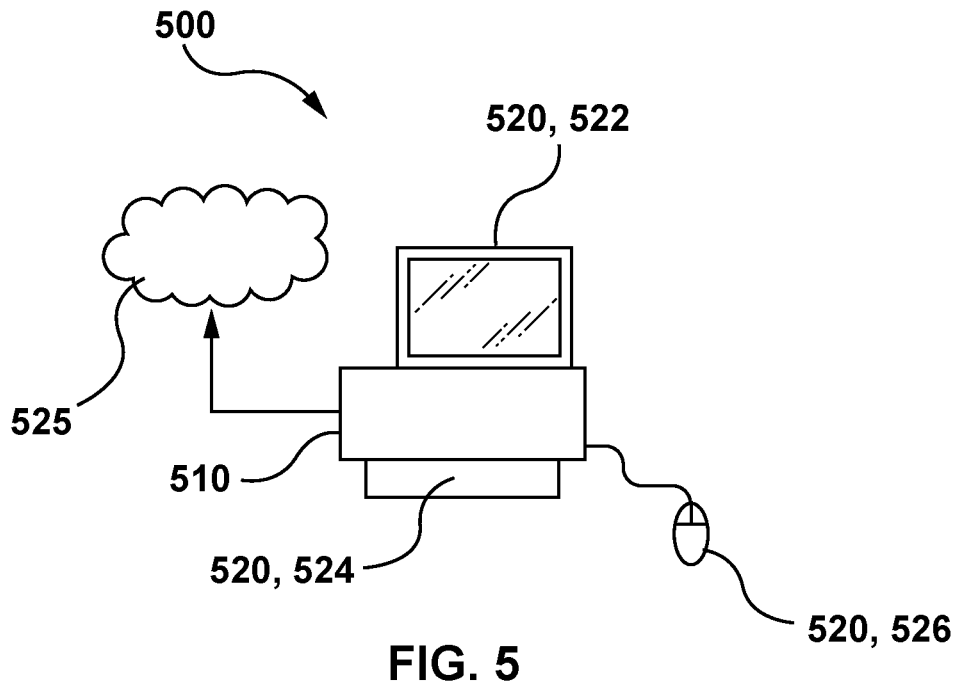
FIG. 5 depicts a schematic diagram of a system for determining an orthodontic treatment, according to certain embodiments of the present technology.
Figure 6:
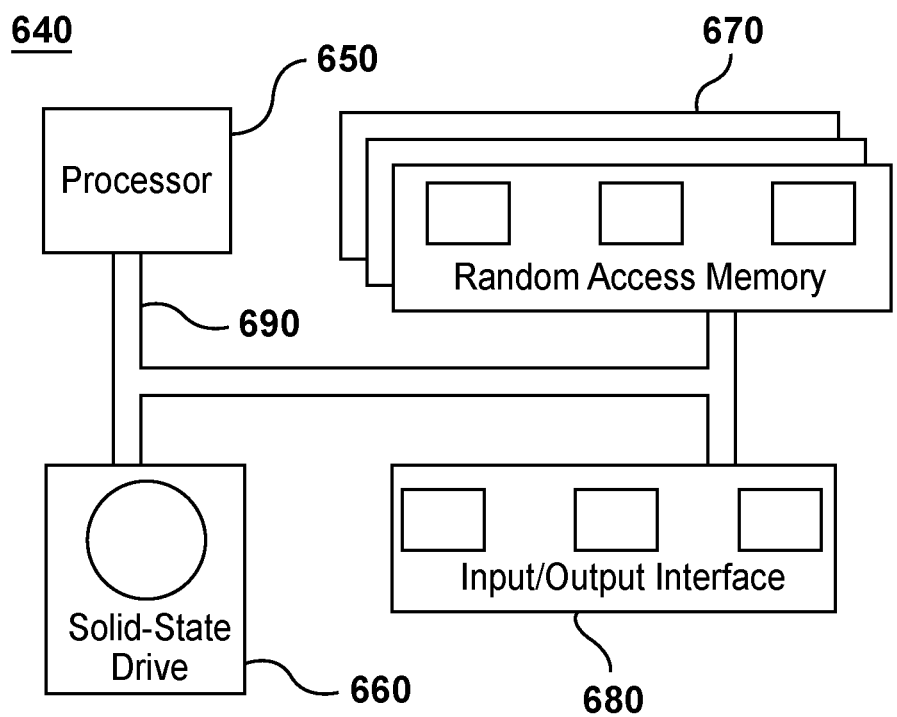
FIG. 6 depicts a sematic diagram of a computing environment of the system of FIG. 5, according to certain embodiments of the present technology.

Now, with reference to FIGS. 5 to 6, there is depicted a schematic diagram of a system 500 suitable for determining the orthodontic treatment for the subject based on the rotation center 406, in accordance with the non-limiting embodiments of the present technology.

It is to be expressly understood that the system 500 as depicted is merely an illustrative implementation of the present technology. Thus, the description thereof that follows is intended to be only a description of illustrative examples of the present technology. This description is not intended to define the scope or set forth the bounds of the present technology. In some cases, what is believed to be helpful examples of modifications to the system 500 may also be set forth below. This is done merely as an aid to understanding, and, again, not to define the scope or set forth the bounds of the present technology. These modifications are not an exhaustive list, and, as a person skilled in the art would understand, other modifications are likely possible. Further, where this has not been done (i.e., where no examples of modifications have been set forth), it should not be interpreted that no modifications are possible and/or that what is described is the sole manner of implementing that element of the present technology. As a person skilled in the art would understand, this is likely not the case. In addition, it is to be understood that the system 500 may provide in certain instances simple implementations of the present technology, and that where such is the case they have been presented in this manner as an aid to understanding. As persons skilled in the art would understand, various implementations of the present technology may be of a greater complexity.

In certain non-limiting embodiments of the present technology, the system 500 of FIG. 5 comprises a computer system 510. The computer system 510 is configured, by pre-stored program instructions, to determine the rotation center 406, based on image data associated with the subject, according to the non-limiting embodiments of the present technology.

To that end, in some non-limiting embodiments of the present technology, the computer system 510 is configured to receive image data pertaining to the subject or to a given orthodontic treatment (such as the 3D model 100 depicted in FIG. 1). The computer system 510 may use the image data for determining the rotation center 406 of the subject. According to some non-limiting embodiments of the present technology, the computer system 510 may receive the image data via local input/output interface (such as USB, as an example). In other non-limiting embodiments of the present technology, the computer system 510 may be configured to receive the image data over a communication network 525, to which the computer system 510 is communicatively coupled.

In some non-limiting embodiments of the present technology, the communication network 525 is the Internet and/or an Intranet. Multiple embodiments of the communication network may be envisioned and will become apparent to the person skilled in the art of the present technology. Further, how a communication link between the computer system 510 and the communication network 525 is implemented will depend, inter alia, on how the computer system 510 is implemented, and may include, but are not limited to, a wire-based communication link and a wireless communication link (such as a Wi-Fi communication network link, a 3G/4G communication network link, and the like).

It should be noted that the computer system 510 can be configured for receiving the image data from a vast range of devices (including a CBCT scanner, an intraoral scanner, a laboratory scanner, and the like). Some such devices can be used for capturing and/or processing data pertaining to maxillofacial and/or cranial anatomy of a subject. In certain embodiments, the image data received from such devices is indicative of properties of anatomical structures of the subject, including: teeth, intraoral mucosa, maxilla, mandible, temporomandibular joint, and nerve pathways, among other structures. In some embodiments, at least some of the image data is indicative of properties of external portions of the anatomical structures, for example dimensions of a gingival sulcus, and dimensions of an external portion of a tooth (e.g., a crown of the tooth) extending outwardly of the gingival sulcus. In some embodiments, the image data is indicative of properties of internal portions of the anatomical structures, for example volumetric properties of bone surrounding an internal portion of the tooth (e.g., a root of the tooth) extending inwardly of the gingival sulcus. Under certain circumstances, such volumetric properties may be indicative of periodontal anomalies which may be factored into an orthodontic treatment plan. In some embodiments, the image data includes cephalometric image datasets. In some embodiments, the image data includes datasets generally intended for the practice of endodontics. In some embodiments, the image data includes datasets generally intended for the practice of periodontics.

The image data may include two-dimensional (2D) data and/or tridimensional data (3D). In certain embodiments, the image data includes at least one dataset derived from one or more of the following imaging modalities: computed tomography (CT), radiography, magnetic resonance imaging, ultrasound imaging, nuclear imaging and optical imaging. Any medical imaging modality is included within the scope of the present technology. In certain embodiments, the image data includes 2D data, from which 3D data may be derived, and vice versa.

Further, it is contemplated that the computer system 510 may be configured for processing of the received image data. The resulting image data received by the computer system 510 is typically structured as a binary file or an ASCII file, may be discretized in various ways (e.g., point clouds, polygonal meshes, pixels, voxels, implicitly defined geometric shapes), and may be formatted in a vast range of file formats (e.g., STL, OBJ, PLY, DICOM, and various software-specific, proprietary formats). Any image data file format is included within the scope of the present technology. For implementing functions described above, the computer system 510 may further comprise a corresponding computing environment.

With reference to FIG. 6, there is depicted a schematic diagram of a computing environment 640 suitable for use with some implementations of the present technology. The computing environment 640 comprises various hardware components including one or more single or multi-core processors collectively represented by a processor 650, a solid-state drive 660, a random access memory 670 and an input/output interface 680. Communication between the various components of the computing environment 640 may be enabled by one or more internal and/or external buses 690 (e.g. a PCI bus, universal serial bus, IEEE 1394 "Firewire" bus, SCSI bus, Serial-ATA bus, ARINC bus, etc.), to which the various hardware components are electronically coupled.

The input/output interface 680 allows enabling networking capabilities such as wire or wireless access. As an example, the input/output interface 680 comprises a networking interface such as, but not limited to, a network port, a network socket, a network interface controller and the like. Multiple examples of how the networking interface may be implemented will become apparent to the person skilled in the art of the present technology.

For example, but without being limiting, the input/output interface 680 may implement specific physical layer and data link layer standard such as Ethernet™, Fibre Channel, Wi-Fi™ or Token Ring. The specific physical layer and the data link layer may provide a base for a full network protocol stack, allowing communication among small groups of computers on the same local area network (LAN)

and large-scale network communications through routable protocols, such as Internet Protocol (IP).

According to implementations of the present technology, the solid-state drive 660 stores program instructions suitable for being loaded into the random access memory 670 and executed by the processor 650, according to certain aspects and embodiments of the present technology. For example, the program instructions may be part of a library or an application.

In these embodiments, the computing environment 640 is implemented in a generic computer system which is a conventional computer (i.e. an "off the shelf" generic computer system). The generic computer system may be a desktop computer/personal computer, but may also be any other type of electronic device such as, but not limited to, a laptop, a mobile device, a smart phone, a tablet device, or a server.

As persons skilled in the art of the present technology may appreciate, multiple variations as to how the computing environment 640 is implemented may be envisioned without departing from the scope of the present technology.

Referring back to FIG. 5, the computer system 510 has at least one interface device 520 for providing an input or an output to a user of the system 500, the interface device 520 being in communication with the input/output interface 680. In the embodiment of FIG. 5, the interface device is a screen 522. In other embodiments, the interface device 520 may be a monitor, a speaker, a printer or any other device for providing an output in any form such as image-form, written form, printed form, verbal form, 3D model form, or the like.

In the embodiment of FIG. 5, the interface device 520 also comprises a keyboard 524 and a mouse 526 for receiving input from the user of the system 500. Other interface devices 520 for providing an input to the computer system 510 can include, without limitation, a USB port, a microphone, a camera or the like.

The computer system 510 may be connected to other users, such as through their respective clinics, through a server (not depicted). The computer system 510 may also be connected to stock management or client software which could be updated with stock when the orthodontic treatment has been determined and/or schedule appointments or follow-ups with clients, for example.

Determining Rotation Center

As alluded to above, according to the non-limiting embodiments of the present technology, the rotation center 406 of the mandible 204 associated with the subject may be determined by the processor 650 of the computing environment 640. To that end, first, the processor 650 may be configured to receive image data associated with the skull 200.

Figure 7:
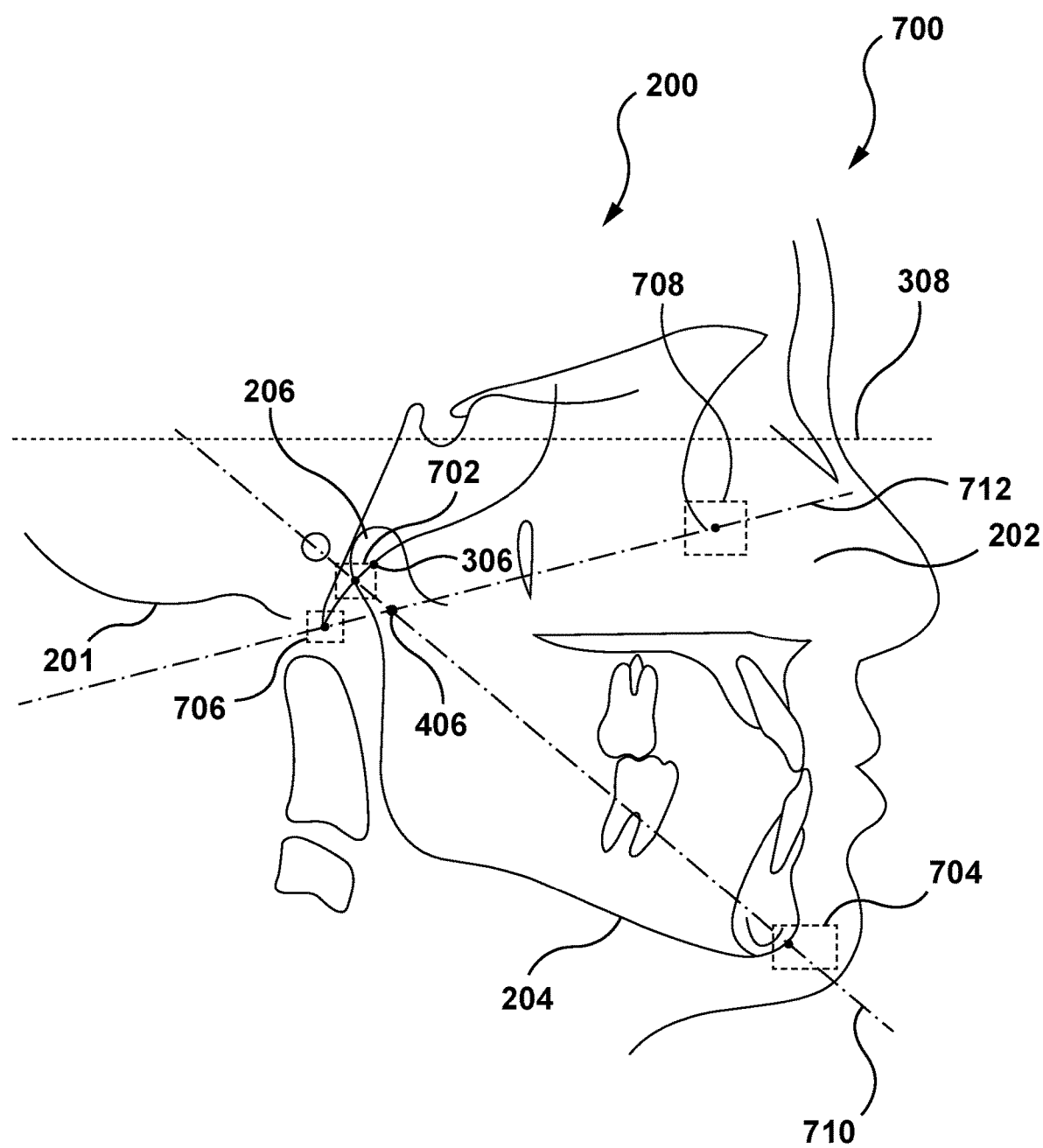
FIG. 7 schematically depicts a lateral image of a first side of a subject's skull used, by a processor of the computing environment of FIG. 6, for determining a rotation center of a subject's mandible, according to the non-limiting embodiments of the present technology.

With reference to FIG. 7, there is depicted a schematic diagram of a lateral image 700 of a first side of the skull 200 used, by the processor 650, for determining the rotation center 406, in accordance with the non-limiting embodiments of the present technology.

In the non-limiting embodiments of the present technology, the processor 650 has been configured to generate the lateral image 700 based on the received image data associated with the skull 200.

In some non-limiting embodiments of the present technology, the image data associated with the skull 200 may comprise a 3D image of the skull 200, such as a CT scan, and/or a magnetic resonance scan. In other non-limiting embodiments of the present technology, the image data associated with the skull 200 may comprise a 2D image, for example, but not limited to, a radiograph and/or a photograph.

In specific non-limiting embodiments of the present technology, the radiograph may further comprise a teleroentgenogram (TRG), which provides a lateral image of one of the first side and a second side (not separately depicted) of the skull 200.

Further, in order to determine the rotation center 406, the processor 650 may be configured to identify, using the lateral image 700, certain reference points on the skull 200. To that end, according to the non-limiting embodiments of the present technology, the processor 650 may be configured to determine the rotation center 406 as an intersection of reference lines, in the lateral image 700, having been generated based on the identified reference points on the skull 200.

In the non-limiting embodiments of the present technology, the processor 650 is configured to identify, in the lateral image 700, at least two pairs of reference points to generate, based on each pair of reference points, a respective reference line.

In some non-limiting embodiments of the present technology, the processor 650 may be configured to identify, for a first pair of reference points, a first reference point 702 and a second reference point 704. According to some non-limiting embodiments of the present technology, the processor 650 is configured to identify the first reference point 702 to be located on the cranial portion 201 of the skull 200, and the second reference point 704—to be located on the mandible 204 of the skull 200. Accordingly, the processor 650 may be further configured to generate, in the lateral image 700, a first reference line 710 as a line extending through the first reference point 702 and the second reference point 704.

In specific non-limiting embodiments of the present technology, as the first reference point 702, the processor 650 may be configured to identify the Articulare point associated with the skull 200; and as the second reference point 704, the processor 650 may be configured to identify the Gnathion point associated with the skull 200. Thus, according to these embodiments, the first pair of reference points for generating the first reference line 710 may include the Articulare point and the Gnathion point associated with the skull 200.

Further, in some non-limiting embodiments of the present technology, the processor 650 may be configured to identify a second pair of reference points including a third reference point 706 and a fourth reference point 708 for generating a second reference line 712. According to some non-limiting embodiments of the present technology, the processor 650 is configured to identify the third reference point 706 and the fourth reference point 708 as points, which are both located on the cranial portion 201 of the skull 200.

In specific non-limiting embodiments of the present technology, as the third reference point 706, the processor 650 may be configured to identify the Basion point associated with the skull 200; and as the fourth reference point 708, the processor 650 may be configured to identify the Orbitale point associated with the skull 200. Thus, according to these embodiments, the second pair of reference points for generating the second reference line 712 may include the Basion point and the Orbitale point associated with the skull 200.

It should be expressly understood that approaches to identifying the first reference point 702, the second reference point 704, the third reference point 706, and the fourth reference point 708 are not limited and may include, according to some non-limiting embodiments of the present technology, conducting, by the processor 650, a cephalometric analysis of the image data used for generating the lateral image 700 of the skull 200.

Broadly speaking, the cephalometric analysis, as referred to herein, is an analysis including tracing of dental and skeletal relationships (absolute/relative angles and distances) based on certain anatomical reference points (such as such as the first reference point 702, the second reference point 704, the third reference point 706, and the fourth reference point 708) in bony and soft tissue of a skull (for example, the skull 200). As such, a particular type of the cephalometric analysis of the skull 200 may depend on the image data, associated with the skull 200, having been used, by the processor 650, for generating the lateral image 700.

For example, in those embodiments where the image data associated with the skull 200 is represented by 2D images, for example, a posteroanterior radiograph of the skull 200, the cephalometric analysis may comprise a posteroanterior cephalometric analysis. By the same token, if the image data associated with the skull 200 comprises a lateral radiograph (such as the TRG), the cephalometric analysis may comprise a lateral cephalometric analysis. In yet another example, where the image data associated with the skull 200 is a 3D image thereof (such as a CT scan or a magnet resonance scan), the cephalometric analysis comprises a 3D cephalometric analysis.

Further, according to the non-limiting embodiments of the present technology, the conducting, by the processor 650, the cephalometric analysis may comprise at least (1) segmenting the image data, for example, into a set of contours, within each of which pixels of the image data have similar characteristics (that is, computed properties), such as color, intensity, texture, and the like; (2) placing each of the set of contours into a signal coordinate system, thereby aligning each of the set of contours relative to each other; and (3) detecting the reference points based on predetermined relative positions and distances thereamong. For example, the Basion point, within the skull 200, may be identified, by the processor 650, based on a premise that it is a most anterior point on the foramen magnum (not separately depicted) of the skull 200.

Accordingly, in some non-limiting embodiments of the present technology, for detecting each of the first and the second pairs of reference points, the processor 650 may apply an image filtering approach based on enhancing contrast of radiographic images, and further be configured for locating the reference points therein based on the predetermined relative positions and distances thereamong.

In other non-limiting embodiments of the present technology, the processor 650 may be configured to apply a model-based approach for the detecting the reference points. In these embodiments, the processor 650 may be configured to apply, to the segmented image data associated with the skull 200, techniques, such as, but not limited to, pattern matching techniques, spatial spectroscopy techniques, statistical pattern recognition techniques, and the like.

In yet other non-limiting embodiments of the present technology, the detecting the reference points may comprise applying, by the processor 650, one or more machine-learning algorithms, such as, but not limited to, a pulsed coupled neural networks, support vector machines, and the like. In these embodiments, a given machine-learning algorithm is first trained based on a training set of data preliminarily annotated (labelled), for example, by human assessors, for further identifying specific reference points based on certain image data associated with the skull 200. It can be said that, in these embodiments, the predetermined relative positions and distances among the reference points are learnt, by the processor 650, based on the training set of data including various image data associated with different skulls. Unsupervised implementations (that is, those not including labelling data in the training set of data) of machine-learning algorithms may also be applied, by the processor 650, without departing from the scope of the present technology.

Thus, having identified the first reference point 702, the second reference point 704, the third reference point 706, and the fourth reference point 708, and, based thereon, generated the first reference line 710 and the second reference line 712, the processor 650 is further configured to determine the rotation center 406 as an intersection thereof as depicted in FIG. 7.

As it can be appreciated from FIG. 7, the so determined rotation center 406 of the mandible 204 is located in the mandibular head 206, in the lateral image 700, lower and more posteriorly relative to the geometric center 306 of the mandibular head 206.

Determining Orthodontic Treatment

According to the non-limiting embodiments of the present technology, the processor 650 may further be configured to determine, based on the rotation center 406, the orthodontic treatment for the subject. To that end, the processor 650 may be configured, based at least on the rotation center 406 and the 3D model 100, to reproduce a model of the mandible 204 of the skull 200 for further determining a rotation axis thereof. Further, the processor 650 may be configured to use the rotation axis for reproducing at least some of the movements of the mandible 204 described above with respect to FIGS. 2 to 4.

Figure 8:
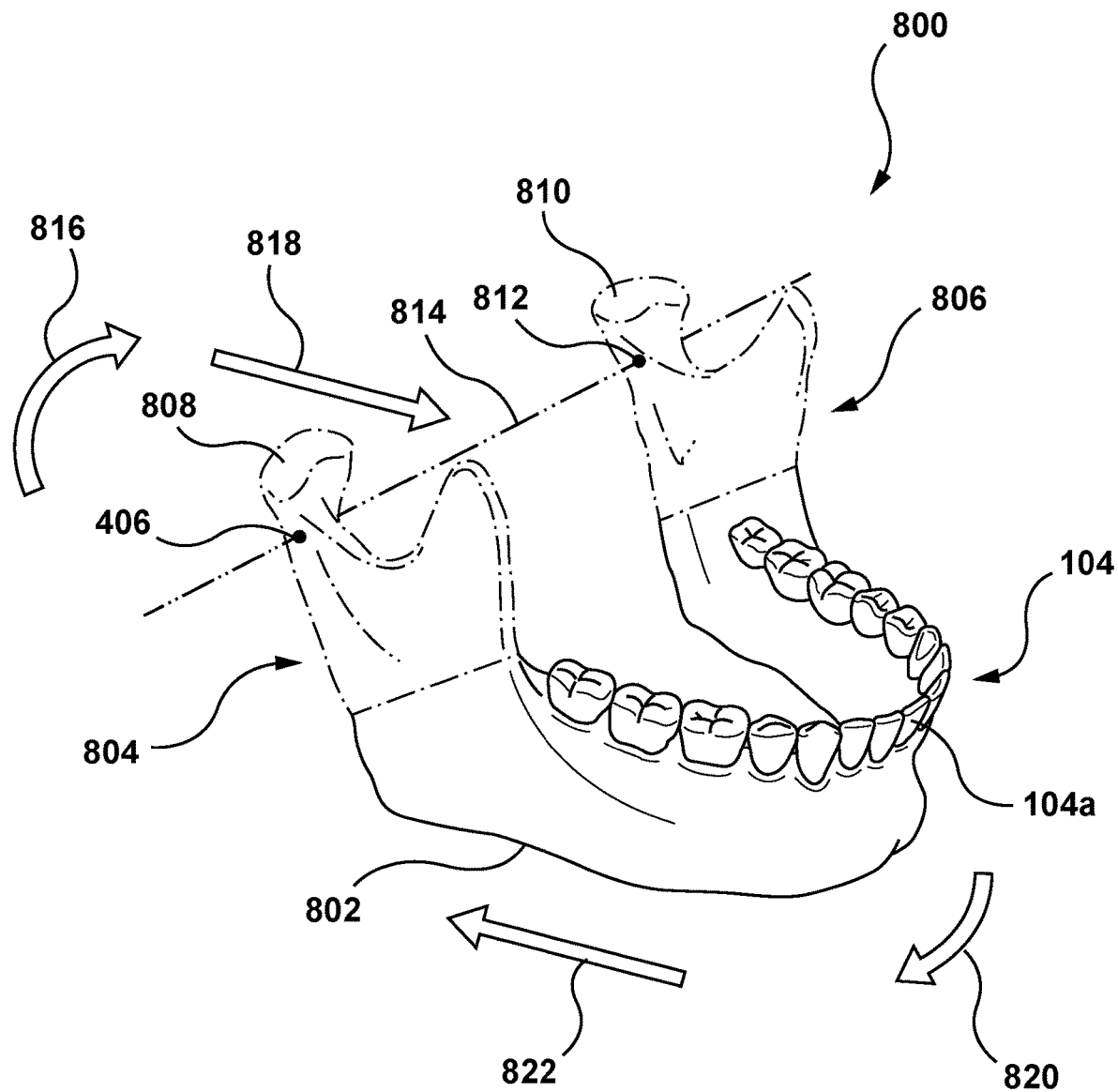
FIG. 8 depicts a mandible model generated, by the processor of the computing environment of FIG. 6, based on the determined rotation center for determining the orthodontic treatment, according to the non-limiting embodiments of the present technology.

With reference to FIG. 8, there is depicted a mandible model 800 of the mandible 204 having been generated, by the processor 650, based at least on the representation lower arch form 104 of the subject and the rotation center 406 of the mandible 204, in accordance with the non-limiting embodiments of the present technology.

As can be appreciated from FIG. 8, the mandible model 800 includes a mandible model body 802 having been generated, by the processor 650, based on the 3D model of the lower arch form 104 of the subject; a first mandible model ramus 804 including a first mandibular head model 808 of the mandibular head 206; and a second mandible model ramus 806 including a second mandibular head model 810.

In some non-limiting embodiments of the present technology, the processor 650 has been configured to generate the first mandible model ramus 804 including the first mandibular head model 808 based on the rotation center 406. Further, the processor 650 may be configured to generate, based on the rotation center 406, a rotation axis 814.

In some non-limiting embodiments of the present technology, the processor 650 may be configured to generate the rotation axis 814 for the mandible model 800 to extend through the rotation center 406 and parallel to the horizontal plane 308 associated with the skull 200 (not separately depicted).

In other non-limiting embodiments of the present technology, the processor 650 may be configured to generate the rotation axis 814 for the mandible model 800 based on the rotation center 406 and a second rotation center 812. To that end, the processor 650 may have been configured to generate a lateral image of a second side of the skull 200 and determine the second rotation center 812 according to the description above given in respect of FIG. 7. Accordingly, based on the second rotation center 812, the processor 650 may have been configured to generate the second mandible model ramus 806 including the second mandibular head model 810. Finally, the processor 650 may be configured to generate the rotation axis 814 for the mandible model 800 as a line extending through the rotation center 406 and the second rotation center 812 in the first mandibular head model 808 and the second mandibular head model 810, respectively.

Thus, referring back to FIG. 1 and with continued reference to FIG. 8, according to the non-limiting embodiments of the present technology, based on the so generated mandible model 800 including the rotation axis 814, the processor 650 may be further configured to reproduce at least some of the movements of the mandible 204 indicative of the articulation thereof, as discussed above with reference to FIGS. 2 to 4, on the 3D model 100, specifically, movements of the lower arch form 104 relative to the upper arch form 102.

For example, the processor 650 may reproduce simultaneous translational and rotational movements of the lower arch form 104, as described with reference to FIG. 4 in respect of the mandible 204. Specifically, when the first mandibular head model 808 is moving around the rotation axis 814 rotationally clockwise in a first direction 816 and translationally forward in a second direction 818, the lower arch form 104 will be moving rotationally counterclockwise in a third direction 820 and translationally backwards in a fourth direction 822. Also, as previously mentioned, based on these movements, certain diagnostic parameters for devising the orthodontic treatment can be considered.

Figure 9:
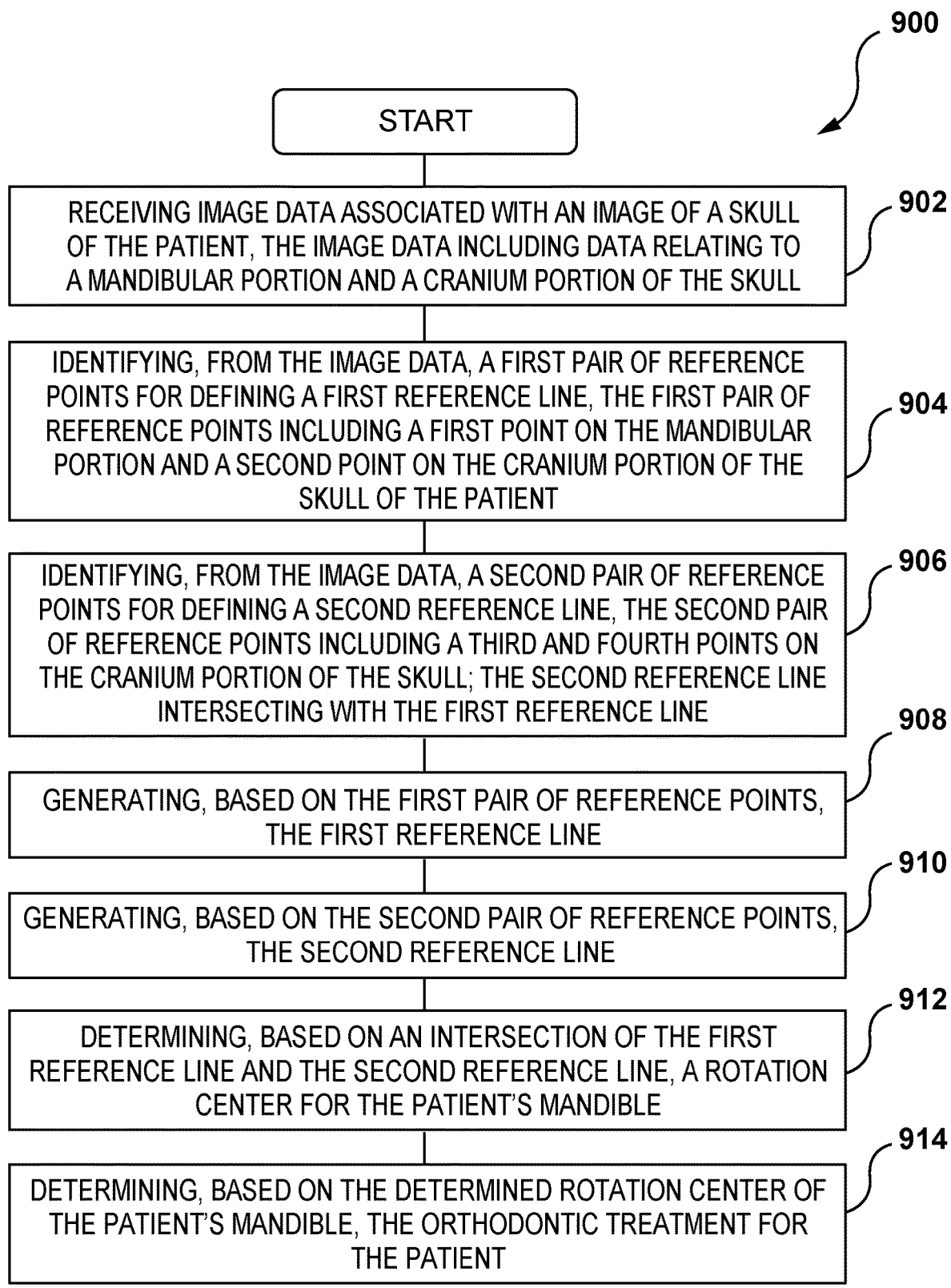
FIG. 9 depicts a flowchart of a method for determining the orthodontic treatment for the subject, according to the non-limiting embodiments of the present technology.

Given the architecture and the examples provided hereinabove, it is possible to execute a method for determining an orthodontic treatment for a subject. With reference to FIG. 9, there is depicted a flowchart of a method 900, according to the non-limiting embodiments of the present technology. The method 900 can be executed by a processor of a computing environment, such as the processor 650 of the computing environment 640.

According to the non-limiting embodiments of the present technology, the processor 650 is configured to determine the orthodontic treatment based on a rotation center of a subject's mandibular jaw (for example, the rotation center 406 of the mandible 204 as described above with reference to FIG. 4).

Step 902—Receiving Image Data Associated with an Image of a Skull of the Patient, the Image Data Including Data Relating to a Mandibular Portion and a Cranium Portion of the Skull The method 900 commences at step 902 where the processor 650 is configured to receive image data associated with a subject's skull (such as the skull 200 depicted in FIGS. 2 to 4).

In the non-limiting embodiments of the present technology, the processor 650 may be configured to receive a 3D image of the skull 200, such as a CT scan, and/or a magnetic resonance scan. In other non-limiting embodiments of the present technology, the image data associated with the skull 200 may comprise a 2D image, for example, but not limited to, a radiograph and/or a photograph.

In specific non-limiting embodiments of the present technology, the radiograph may further comprise a teleroentgenogram (TRG).

Further, according to the non-limiting embodiments of the present technology, the processor 650 can be configured to generate, based on the received image data, a lateral image of at least one of the first and the second sides of the skull 200 (such as the lateral image 700 depicted in FIG. 7 and described with reference thereto).

According to the non-limiting embodiments of the present technology, the lateral image 700 is further used, by the processor 650, for identifying specific reference points associated with the skull 200. Based on the identified reference points, the processor 650 may further be configured to determine the rotation center 406 of the mandible 204.

The method 900 hence advances to step 904.

Step 904—Identifying, from the Image Data, a First Pair of Reference Points for Defining a First Reference Line, the First Pair of Reference Points Including a First Point on the Mandibular Portion and a Second Point on the Cranium Portion of the Skull of the Patient At step 904, the processor 650 is configured, using the lateral image 700, to identify a first pair of reference points, for example, the first reference point 702 and the second reference point 704 as described above with reference to FIG. 7.

According to the non-limiting embodiments of the present technology, the processor 650 is configured to identify the first reference point 702 as a point located on the cranial portion 201 of the skull 200; and identify the second reference point 704 as a point located on the mandible 204.

In specific non-limiting embodiments of the present technology, as the first reference point 702, the processor 650 can be configured to identify the Articulare point associated with the skull 200; and as the second reference point 704, the processor 650 can be configured to identify the Gnathion point associated with the skull 200.

According to the non-limiting embodiments of the present technology, in order to identify the reference points (such as the first reference point 702 and the second reference point 704), the processor 650 may be configured to conduct a cephalometric analysis of the image data used for generating the lateral image 700. In certain non-limiting embodiments of the present technology, the processor 650 may be configured to conduct the cephalometric analysis of the lateral image 700.

As described above with reference to FIG. 7, the cephalometric analysis allows for automatically tracing of dental and skeletal relationships (absolute/relative angles and distances) based on certain anatomical reference points in bony and soft tissue of the skull 200.

According to the non-limiting embodiments of the present technology, the conducting, by the processor 650, the cephalometric analysis can comprise at least (1) segmenting the image data, for example, into a set of contours, within each of which pixels of the image data have similar characteristics (such as color, intensity, texture, and the like); (2) placing each of the set of contours into a signal coordinate system, thereby aligning each of the set of contours relative to each other; and (3) detecting the reference points based on predetermined relative positions and distances thereamong.

According to the non-limiting embodiments of the present technology, for detecting the reference points associated with the skull 200, the processor 650 can be configured to apply at least one of an image filtering approach, a model-based approach, and a machine-learning approach, as described above with reference to FIG. 7.

Having determined the first pair of reference points, the method 900 advances to step 906.

Step 906—Identifying, from the Image Data, a Second Pair of Reference Points for Defining a Second Reference Line, the Second Pair of Reference Points Including a Third and Fourth Points on the Cranium Portion of the Skull; the Second Reference Line Intersecting with the First Reference Line At step 906, via conducting the cephalometric analysis as described above, the processor 650 is configured to identify a second pair of reference points. For example, the processor 650 may be configured to identify the third reference point 706 and the fourth reference point 708. According to the non-limiting embodiments of the present technology, the processor 650 may be configured identify the third reference point 706 and the fourth reference point 708 both to be located on the mandible 204.

In specific non-limiting embodiments of the present technology, as the third reference point 706, the processor 650 may be configured to identify the Basion point associated with the skull 200; and as the fourth reference point 708, the processor 650 may be configured to identify the Orbitale point associated with the skull 200.

Having determined the second pair of reference points, the method 900 advances to step 906.

Step 908—Generating, Based on the First Pair of Reference Points, the First Reference Line According to the non-limiting embodiments of the present technology, in order to determine the rotation center 406, the processor 650 is configured to generate reference lines based on the so identified reference points. Thus, at step 908, the processor 650 is configured to generate, based on the first pair of reference points (that is, the first reference point 702 and the reference point 704), the first reference line 710, as described above with reference to FIG. 7.

Thus, in specific non-limiting embodiments of the present technology, the first reference line 710 is extending through the Articulare point and the Gnathion point associated with the skull 200.

Step 910—Generating, Based on the Second Pair of Reference Points, the Second Reference Line At step 910, the processor 650 is configured to generate a second reference line, based on the second pair of reference points, which are the third reference point 706 and the fourth reference point 708. For example, the processor 650 can be configured to generate the second reference line 712, as described above with reference to FIG. 7.

Thus, in specific non-limiting embodiments of the present technology, the second reference line 712 is extending through the Basion point and the Orbitale point associated with the skull 200.

Having generated the first reference line 710 and the second reference line 712, the method 900 advances to step 912.

Step 912—Determining, Based on an Intersection of the First Reference Line and the Second Reference Line, a Rotation Center for the Patient's Mandible At step 912, according to the non-limiting embodiments of the present technology, the processor 650 is configured to determine the rotation center 406 of the mandible 204 based on the so generated the first reference line 710 and the second reference line 712. To that end, the processor 650 is configured to determine the rotation center 406 as an intersection of the first reference line 710 and the second reference line 712, as depicted in FIG. 7.

As can be appreciated from FIG. 7, the so determined rotation center 406 is located lower and more posteriorly than the geometric center 306 of the mandibular head 206 of the mandible 204.

The method 900 hence advances to step 914.

Step 914—Determining, Based on the Determined Rotation Center of the Patient's Mandible, the Orthodontic Treatment for the Patient At step 914, according to the non-limiting embodiments of the present technology, the processor 650 is configured to determine the orthodontic treatment for the subject based at least on the so determine rotation center 406 and a 3D model of subject's arch forms (for example, the 3D model 100 depicted in FIG. 1).

According to the non-limiting embodiments of the present technology, the determining the orthodontic treatment for the subject can comprise determining, based on the rotation center 406, movements of the lower arch form 104 relative to the upper arch form 102 of the subject. In this regard, the processor 650 may be configured to determine a rotation axis (such as the rotation axis 814 depicted in FIG. 8) for the lower arch form 104.

To that end, the processor 650 can be configured to generate a model of the mandible 204 of the subject based on the 3D model 100 and the rotation center 406—for example the mandible model 800 depicted in FIG. 8.

As can be appreciated form FIG. 8, the mandible model 800 comprises the mandible model body 802, generated based on the lower arch form 104; and the first mandible model ramus 804 including the first mandibular head model 808 of the mandibular head 206, generated based on the rotation center 406. Thus, in some non-limiting embodiments of the present technology, the processor 650 may be configured to determine the rotation axis 814 as a line extending through the rotation center 406 and being parallel to the horizontal plane 308 of the skull 200.

In other non-limiting embodiments of the present technology, the processor 650 may be configured to determine a second rotation center of the mandible 204 (for example, the second rotation center 812). To that end, the processor 650 may be configured, based on the received image data associated with the subject, to generate the second lateral image of the second side (not separately depicted) of the skull 200 and apply, mutatis mutandis, the approach for determining the rotation center 406 described above. Further, the processor 650 may be configured, based on the determined second rotation center 812, to generate the second mandible model ramus 806 including the second mandibular head model 810.

Thus, the processor 650 may be configured to determine the rotation axis 814 as a line extending through the rotation center 406 and the second rotation center 812 located in the first mandibular head model 808 and the second mandibular head model 810, respectively.

Accordingly, by doing so, the processor 650 can be said to be configured to transfer at least some of the articulation movements of the mandible 204 described above with reference to FIGS. 2 to 4 onto the lower arch form 104 for reproducing its movements relative to the upper arch form 102.

Thus, certain embodiments of the method 900 allow for reproducing, based on the rotation center 406, kinematics of the lower arch form 104 of the subject which are realistic and effectively account for rotational and translational components thereof using only 2D image data, in the absence of CT or magnetic resonance scans of the skull 200. Further, the present technology allows for determining the rotation center 406 individually for the subject, based on specifically determined reference points associated with the skull 200 as the first reference point 702, the second reference point 704, the third reference point 706, and the fourth reference point 708 may be indicative of muscle attachments of the muscles aiding in effectuating the movements of the mandible 204 uniquely associated with the subject. Thus, some embodiments of the present technology are directed to more efficient methods and systems for determining individualized orthodontic treatment.

The method 900 hence terminates.

It should be expressly understood that not all technical effects mentioned herein need to be enjoyed in each and every embodiment of the present technology.

Modifications and improvements to the above-described implementations of the present technology may become apparent to those skilled in the art. The foregoing description is intended to be exemplary rather than limiting. The scope of the present technology is therefore intended to be limited solely by the scope of the appended claims.

The invention claimed is:

1. A method for determining an orthodontic treatment for a patient, the method being executable by a processor, the method comprising:
   receiving image data, the image data being associated with an image of a skull of the patient, the image data including data relating to a mandibular portion and a cranium portion of the skull;
   identifying, from the image data, a first pair of reference points for defining a first reference line, the first pair of reference points including an Articulare point and a Gnathion point of the skull of the patient;
   identifying, from the image data, a second pair of reference points for defining a second reference line, the second pair of reference points including a Basion point and an Orbitale point of the skull; the second reference line intersecting with the first reference line;
   generating, based on the first pair of reference points, the first reference line;
   generating, based on the second pair of reference points, the second reference line;
   determining, based on an intersection of the first reference line and the second reference line, a rotation center for a patient's mandible;
   determining, based on the rotation center of the patient's mandible, the orthodontic treatment for the patient.

2. The method of claim 1, wherein the identifying the first and second pairs of reference points comprises conducting a cephalometric analysis of the image data.

3. The method of claim 2, wherein the cephalometric analysis comprises processing the image data based on one or more of: image segmentation, image alignment, facial landmark detection, and predetermined relative positions between anatomical landmarks.

4. The method of claim 1, wherein the image comprises one or more of: a radiograph, a photograph, a CT scan, a dental model, and a magnetic resonance image.

5. The method of claim 1, wherein the image is a lateral image of a first side of the skull of the patient.

6. The method of claim 5, wherein the rotation center is a first rotation center of the first side of the skull of the patient, and wherein the method further comprises determining a second rotation center based on an image of a second side of the skull of the patient, and wherein the determining the orthodontic treatment is based on the first rotation and the second rotation center.

7. The method of claim 1, wherein the rotation center is not a center of a mandibular head.

8. The method of claim 1, further comprising sending instructions to display, on a screen, the image of at least a portion of the skull and including the rotation center of the mandible.

9. A method for generating a visualization of a skull of a patient including a rotation center of a mandible, the method being executable by a processor, the method comprising:
   receiving image data, the image data being associated with an image of a skull of the patient;
   identifying, from the image data, a first pair of reference points for defining a first reference line, the first pair of reference points including an Articulare point and a Gnathion point of the skull of the patient;
   identifying, from the image data, a second pair of reference points for defining a second reference line, the second pair of reference points including a Basion point and an Orbitale point of the skull; the second reference line intersecting with the first reference line;
   generating, based on the first pair of reference points, the first reference line;
   generating, based on the second pair of reference points, the second reference line;
   determining, based on an intersection of the first reference line and the second reference line, a rotation center for a patient's mandible;
   sending instructions to display, on a screen, the image of the skull including the rotation center for the patient's mandible.

10. A system for determining an orthodontic treatment for a patient, the system comprising a computer system having a processor arranged to execute a method comprising:
    receiving image data, the image data being associated with an image of a skull of the patient;
    identifying, from the image data, a first pair of reference points for defining a first reference line, the first pair of reference points including an Articulare point and a Gnathion point of the skull of the patient;
    identifying, from the image data, a second pair of reference points for defining a second reference line, the second pair of reference points including a Basion point and an Orbitale point of the skull; the second reference line intersecting with the first reference line;
    generating, based on the first pair of reference points, the first reference line;
    generating, based on the second pair of reference points, the second reference line;
    determining, based on an intersection of the first reference line and the second reference line, a rotation center for a patient's mandible;
    determining, based on the rotation center of the patient's mandible, the orthodontic treatment for the patient.

11. The system of claim 10, wherein the identifying the first and second pairs of reference points comprises conducting a cephalometric analysis of the image data.

12. The system of claim 11, wherein the image is a lateral image of a first side of the patient's skull of the patient, and wherein the rotation center is a first rotation center of the first side of the skull of the patient, and wherein the system further comprises determining a second rotation center based on an image of a second side of the skull of the patient, and wherein the determining the orthodontic treatment is based on the first rotation and the second rotation center.

13. The system of claim 10, wherein the rotation center is not a center of a mandibular head.

14. A system for generating a visualization of a skull of a patient including a rotation center of a mandible, the system comprising:
    a screen on which the visualization of the skull of the patient including the rotation center of the mandible is displayed, and a processor connected to the screen and arranged to execute, the method comprising:

receiving image data, the image data being associated with an image of a skull of the patient;

identifying, from the image data, a first pair of reference points for defining a first reference line, the first pair of reference points including an Articulare point and a Gnathion point of the skull of the patient;

identifying, from the image data, a second pair of reference points for defining a second reference line, the second pair of reference points including a Basion point and an Orbitale point of the skull; the second reference line intersecting with the first reference line;

generating, based on the first pair of reference points, the first reference line;

generating, based on the second pair of reference points, the second reference line;

determining, based on an intersection of the first reference line and the second reference line, a rotation center for a patient's mandible;

sending instructions to display, on a screen, the image of the skull including the rotation center for the patient's mandible.

* * * * *